(12) United States Patent
Takahashi et al.

(10) Patent No.: US 10,416,321 B2
(45) Date of Patent: Sep. 17, 2019

(54) X-RAY DIAGNOSTIC APPARATUS

(71) Applicant: Canon Medical Systems Corporation, Otawara-shi (JP)

(72) Inventors: Akihito Takahashi, Nasushiobara (JP); Haruki Iwai, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/921,185

(22) Filed: Mar. 14, 2018

(65) Prior Publication Data

US 2018/0267176 A1    Sep. 20, 2018

(30) Foreign Application Priority Data

Mar. 15, 2017    (JP) .................................. 2017-049483
Mar. 13, 2018    (JP) .................................. 2018-045950

(51) Int. Cl.
| | | |
|---|---|---|
| *G01T 1/20* | (2006.01) | |
| *A61B 6/00* | (2006.01) | |
| *G01T 1/29* | (2006.01) | |
| *G01T 1/208* | (2006.01) | |

(52) U.S. Cl.
CPC ............ *G01T 1/208* (2013.01); *A61B 6/4208* (2013.01); *A61B 6/4266* (2013.01); *G01T 1/20* (2013.01); *G01T 1/2018* (2013.01); *G01T 1/2985* (2013.01); *A61B 6/4441* (2013.01); *A61B 6/463* (2013.01); *A61B 6/5205* (2013.01)

(58) Field of Classification Search
CPC ... A61B 6/4208; A61B 6/4266; A61B 6/4411; A61B 6/463; A61B 6/5205; G01T 1/20; G01T 1/2018; G01T 1/208; G01T 1/2985
See application file for complete search history.

(56) References Cited

U.S. PATENT DOCUMENTS

| | | | |
|---|---|---|---|
| 2014/0103220 A1 | 4/2014 | Ohta et al. | |
| 2015/0003584 A1 | 1/2015 | Weisfield et al. | |
| 2015/0199121 A1* | 7/2015 | Gulaka | G16H 40/63 |
| | | | 715/771 |
| 2016/0278722 A1* | 9/2016 | Tagawa | A61B 6/587 |

FOREIGN PATENT DOCUMENTS

| | | |
|---|---|---|
| JP | 2004-16503 | 1/2004 |
| JP | 2012-223629 | 11/2012 |
| JP | 2014-193192 | 10/2014 |
| WO | WO 2013/015016 A1 | 1/2013 |

* cited by examiner

*Primary Examiner* — Mark R Gaworecki
(74) *Attorney, Agent, or Firm* — Oblon, McClelland, Maier & Neustadt, L.L.P.

(57) ABSTRACT

An X-ray diagnostic apparatus comprises an X-ray detector including a first detector and a second detector capable of simultaneously detecting X-rays irradiated from an X-ray tube, and processing circuitry configured to, when displaying one of a first image based on output from the first detector and a second image based on output from the second detector on a display, display the other one of the first image and the second image corresponding to a partial region of the one of the first image and the second image.

20 Claims, 11 Drawing Sheets

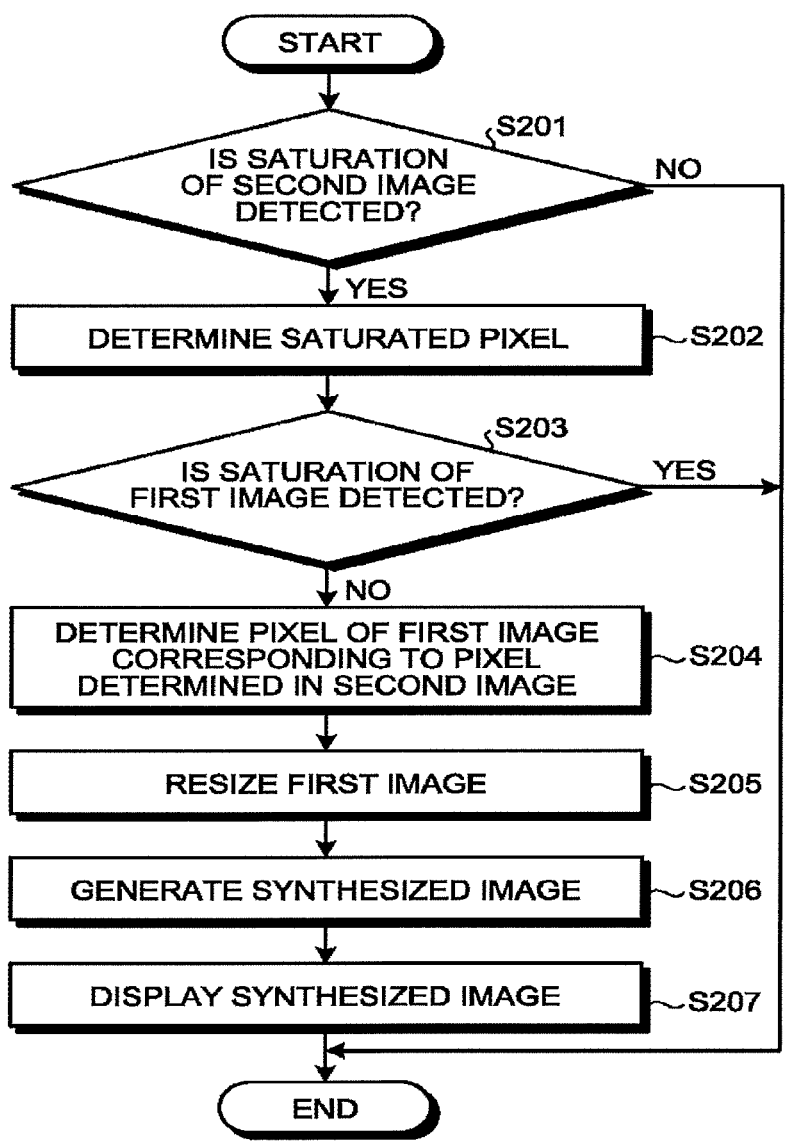

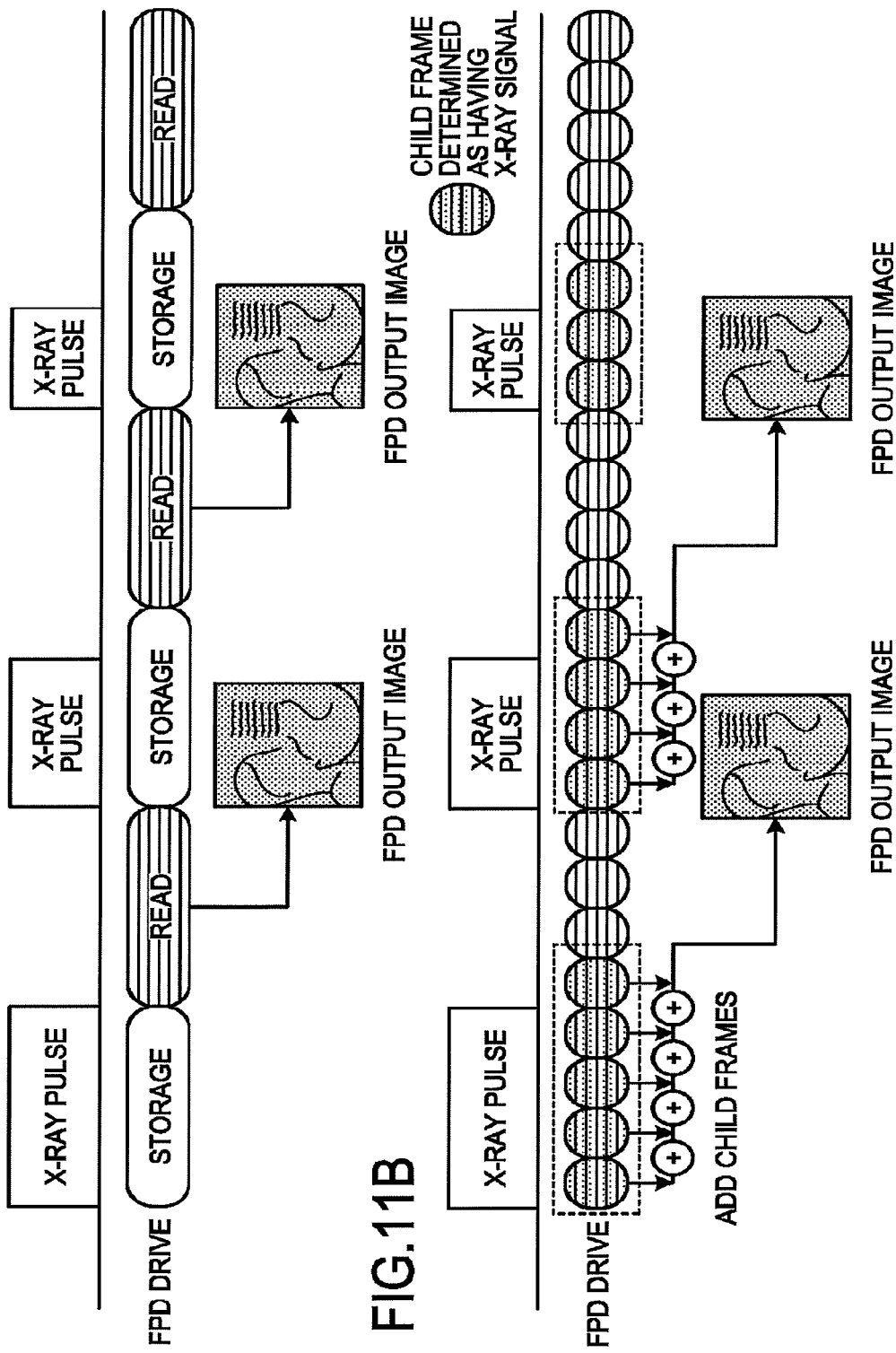

X-RAY DIAGNOSTIC APPARATUS

CROSS-REFERENCE TO RELATED APPLICATIONS

This application is based upon and claims the benefit of priority from Japanese Patent Application No. 2017-49483, filed on Mar. 15, 2017; and Japanese Patent Application No. 2018-045950, filed on Mar. 13, 2018, the entire contents of which are incorporated herein by reference.

FIELD

Embodiments described herein relate generally to an X-ray diagnostic apparatus.

BACKGROUND

Conventionally, in inspection using an X-ray diagnostic apparatus, there is a case where a narrow region of interest is observed with high resolution. In view of this situation, there is a known X-ray diagnostic apparatus including a detector that includes both of a first detector using a thin film transistor (TFT) array and having a large field of view (FOV) part and a second detector using a complementary metal oxide semiconductor (CMOS) and having a smaller FOV and a smaller pixel pitch than those of the first detector.

In such an X-ray diagnostic apparatus, there is a known technology of using the first detector and the second detector by switching depending on the intended use, and displaying one of a first image generated from an X-ray signal output from the first detector and a second image generated from an X-ray signal output from the second detector.

BRIEF DESCRIPTION OF THE DRAWINGS

FIG. 10 is a flowchart illustrating the flow of a process performed by the X-ray image acquirer according to the second embodiment;

FIG. 11A is a diagram for explaining a modification of the second embodiment;

FIG. 11B is a diagram for explaining the modification of the second embodiment.

DETAILED DESCRIPTION

An X-ray diagnostic apparatus comprises an X-ray detector and processing circuitry. The X-ray detector includes a first detector and a second detector capable of simultaneously detecting X-rays irradiated from an X-ray tube. The processing circuitry is configured to, when displaying one of a first image based on output from the first detector and a second image based on output from the second detector on a display, display the other one of the first image and the second image corresponding to a partial region of the one of the first image and the second image.

Exemplary embodiments of the X-ray diagnostic apparatus will be described below with reference to the drawings. Embodiments are not limited to the embodiments described below. Further, the contents of each of the embodiments are, in principle, similarly applicable to any other embodiment.

Figure 1:
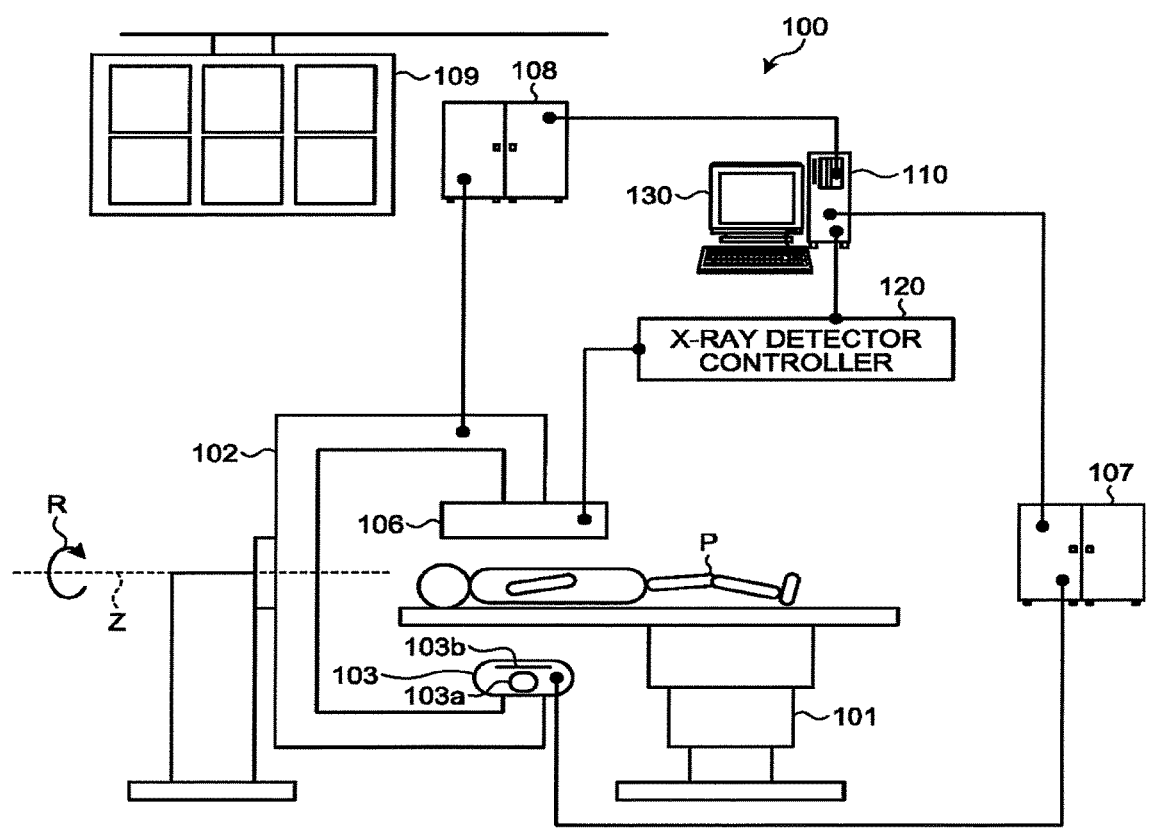
FIG. 1 is a block diagram illustrating a configuration example of an X-ray diagnostic apparatus according to a first embodiment.

FIG. 1 is a block diagram illustrating a configuration example of an X-ray diagnostic apparatus 100 according to a first embodiment. As illustrated in FIG. 1, the X-ray diagnostic apparatus 100 according to the first embodiment includes a catheter bed 101, a holder 102, an X-ray high voltage generator 107, a holder controller 108, a monitor 109, an X-ray image acquirer 110, an X-ray detector (flat panel detector) controller 120, and an input interface 130.

The catheter bed 101 is movable in a vertical direction and a horizontal direction. A subject P is placed on the catheter bed 101. The holder 102 is rotatable in a direction of an arrow R about the Z-axis, and holds an X-ray source 103 and an X-ray detector 106 facing each other.

The X-ray source 103 includes an X-ray tube 103a that irradiates X-rays. The X-ray source 103 further includes an aperture (also referred to as a collimator) and a radiation quality adjustment filter 103b that are used to reduce radiation does to the subject P and improve quality of image data.

Figure 2:
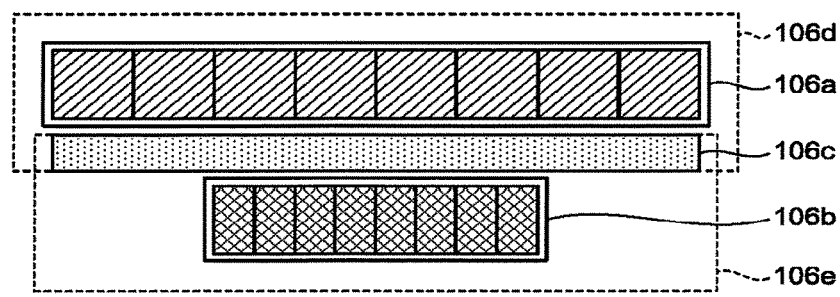
FIG. 2 is a block diagram illustrating a configuration example of an X-ray detector according to the first embodiment.

The X-ray detector (also referred to as a flat panel detector (FPD)) 106 detects X-rays that are irradiated from the X-ray source 103 and transmitted through the subject P. The X-ray detector 106 includes a first detector and a second detector that can simultaneously detect X-rays irradiated from the X-ray source 103. The X-ray detector 106 according to the first embodiment will be described below with reference to FIG. 2. FIG. 2 is a block diagram illustrating a configuration example of the X-ray detector 106 according to the first embodiment.

For example, as illustrated in FIG. 2, the X-ray detector 106 includes a first photodetector 106a, a second photodetector 106b, and a scintillator 106c. The first photodetector 106a and the scintillator 106c constitute a first detector 106d (also referred to as a first FPD), and the second photodetector 106b and the scintillator 106c constitute a second detector 106e (also referred to as a second FPD). The first FPD is one example of the first detector. The second FPD is one example of the second detector. In FIG. 2, the scintillator 106c is arranged so as to be sandwiched between the first photodetector 106a and the second photodetector 106b.

The scintillator 106c converts an X-ray irradiated from the X-ray source 103 into light. The first photodetector 106a includes, for example, a two-dimensional image sensor using a thin film transistor (TFT) array made of amorphous silicon. The first photodetector 106a detects light converted from X-rays by the scintillator 106c and outputs an electrical signal. The second photodetector 106b includes, for example, a two-dimensional image sensor using a complementary metal oxide semiconductor (CMOS) transistor. The second photodetector 106b detects light converted from X-rays by the scintillator 106c and outputs an electrical signal. The electrical signals output by the first photodetector 106a and the second photodetector 106b will be referred to as X-ray signals.

In this manner, the scintillator 106c is shared by the first photodetector 106a and the second photodetector 106b. In other words, the X-ray detector 106 includes the scintillator 106c that converts an X-ray irradiated from the X-ray source 103 into light, and further includes the first photodetector 106a and the second photodetector 106b that share the scintillator 106c, detect the light converted by the scintillator 106c, and output electrical signals. The first photodetector 106a and the second photodetector 106b output the electrical signals that are obtained by simultaneously detecting the light converted by the scintillator 106c.

As illustrated in FIG. 2, the first photodetector 106a and the second photodetector 106b include a plurality of elements as constituent units of pixels. Each of the elements converts a fluorescent image obtained through X-ray incidence into an electric signal, and accumulates the electrical signal in a photo diode (PD). FIG. 2 illustrates a case in which the first photodetector 106a includes eight elements, and the second photodetector 106b includes eight elements.

A pixel pitch of each of the elements of the second photodetector 106b is smaller than a pixel pitch of each of the elements of the first photodetector 106a. In the example illustrated in FIG. 2, the pixel pitch of each of the elements of the first photodetector 106a corresponds to the pixel pitch of two elements of the second photodetector 106b. That is, resolution of the second photodetector 106b is higher than that of the first photodetector 106a. Further, as illustrated in FIG. 2, a FOV size of the first photodetector 106a is larger than that of the second photodetector 106b.

In the second photodetector 106b using the CMOS, a maximum X-ray incident amount tends to be smaller than that of the first photodetector 106a using the amorphous silicon. Therefore, in the second photodetector 106b, even when a high dose of X-rays are irradiated to acquire X-ray image data with a high signal to noise ratio (S/N), it may be difficult to acquire the X-ray image data with the high S/N in some cases.

In the second photodetector 106b, an amount of residual component resulting from incident X-ray (residual components of the electric signal) is smaller than that of the first photodetector 106a. In the first photodetector 106a, a generated electric charge is trapped at a trap level within the photo diode. In contrast, in the second photodetector 106b, an electric charge generated in the photo diode is less trapped due to a characteristic of the CMOS.

Referring back to FIG. 1, the X-ray detector controller 120 controls timing at which the X-ray detector 106 reads an electrical signal. The X-ray detector controller 120 acquires an electrical signal from the X-ray detector 106, generates image data from the acquired electrical signal, and outputs the image data to the X-ray image acquirer 110. Specifically, the X-ray detector controller 120 acquires an electrical signal output from the first FPD, generates first image data (also referred to as a first FPD image or a first image) from the acquired electrical signal, and outputs the first image data to the X-ray image acquirer 110. Further, the X-ray detector controller 120 acquires an electrical signal output from the second FPD, generates second image data (also referred to as a second FPD image or a second image) from the acquired electrical signal, and outputs the second image data to the X-ray image acquirer 110.

The X-ray image acquirer 110 controls the holder controller 108 and the X-ray high voltage generator 107, acquires image data output from the X-ray detector controller 120, and performs image processing on the image data. The X-ray image acquirer 110 acquires image data from both of the first FPD and the second FPD at substantially the same timing. The X-ray image acquirer 110 will be described in detail later.

The X-ray high voltage generator 107 supplies high voltage to the X-ray tube 103a. The holder controller 108 controls rotation of the holder 102 or the like under control of the X-ray image acquirer 110. The monitor 109 displays an X-ray image generated by the X-ray image acquirer 110, or the like. The monitor 109 may be configured with a plurality of sub monitors, or may be configured as a large-screen monitor in which a display region can be arbitrarily divided in accordance with an instruction from an operator. If the monitor 109 includes a plurality of sub monitors, a display region of each of the sub monitors may be arbitrarily divided in accordance with an instruction from the operator. The input interface 130 is a keyboard, a control panel, a foot switch, or the like, and receives input of various kinds of operation on the X-ray diagnostic apparatus 100 from the operator.

The entire configuration of the X-ray diagnostic apparatus 100 according to the first embodiment has been described above. With this configuration, the X-ray diagnostic apparatus 100 according to the first embodiment acquires an X-ray signal output from the X-ray detector 106. The X-ray diagnostic apparatus 100 displays an image generated from the acquired X-ray signal on the monitor 109. For example, the X-ray diagnostic apparatus 100 displays, on the monitor 109, an image that is set by the operator in accordance with a diagnostic site. For example, the X-ray diagnostic apparatus 100 displays the first image and the second image by switching on the monitor 109 in accordance with an instruction from the operator.

Figure 3:
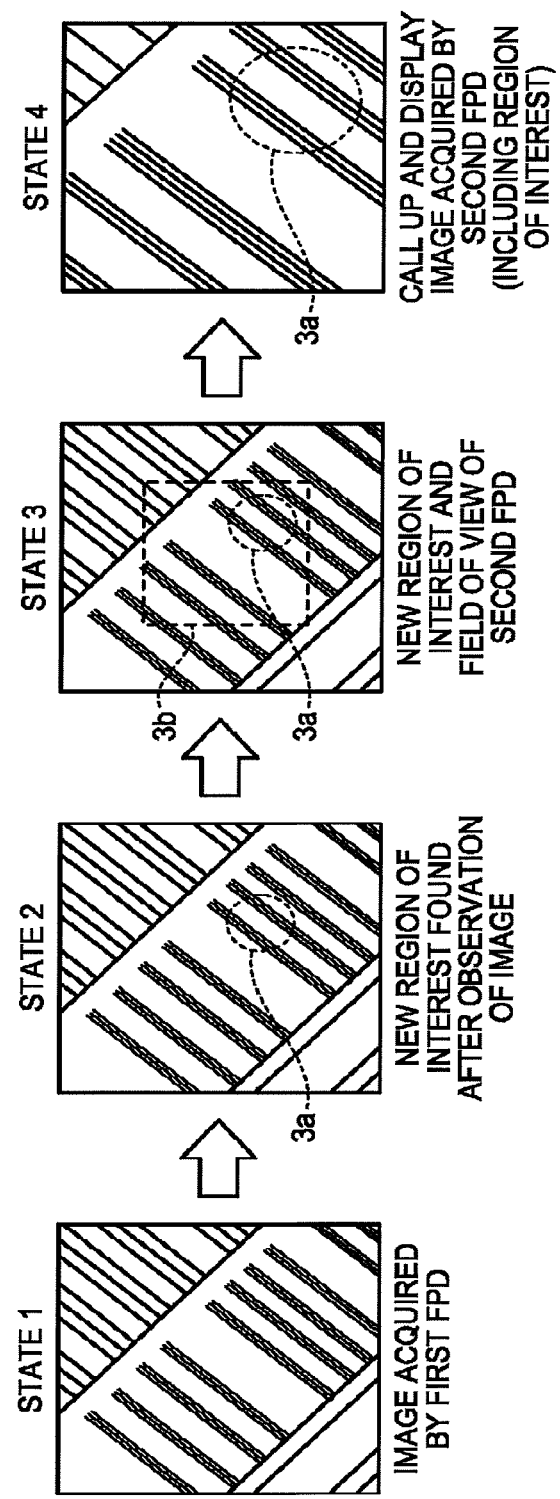
FIG. 3 is a diagram for explaining the first embodiment.

With the X-ray diagnostic apparatus as described above, in an actual clinical procedure, there may be a case where, after an X-ray image acquired for the initial purpose is checked, observation of a target site for a different purpose is required. In such a case, in general, the first image and the second image are acquired again under a desired condition for the different purpose. However, from the standpoint of reducing an X-ray dose to a subject, it is desirable to avoid re-acquisition of images for the different purpose. Further, when the first image is acquired, an electrical signal is also acquired from the second FPD, and, when the second image is acquired, an electrical signal is also acquired from the first FPD. In view of the foregoing situations, in the embodiments described below, when one of the first image generated from the electrical signal output from the first photodetector 106a and the second image generated from the electrical signal output from the second photodetector 106b is displayed on the monitor 109, the other one of the first image and the second image corresponding to a partial region of the one of the first image and the second image is displayed. That is, when displaying one of the first image and the second image on the monitor 109, the X-ray diagnostic apparatus 100 displays the other one of the first image and the second image compensating for a partial region of the one of the first image and the second image. In the X-ray diagnostic apparatus 100 according to the first embodiment, for example, a case will be described in which when the first image generated from an electrical signal output from the first photodetector 106a is displayed on the monitor 109, the second image compensating for a partial region of the first image is displayed. FIG. 3 is a diagram for explaining the first embodiment.

A state 1 in FIG. 3 illustrates an example of the first image that is acquired upon reception of display of the first image. For example, an operator acquires an image and thereafter observes the first image illustrated in the state 1 in FIG. 3. In some cases, when the operator observes the first image, the operator desires to observe a new region of interest as illustrated in a state 2 in FIG. 3, for example. A region 3a enclosed by a dashed line in the state 2 in FIG. 3 indicates a region of interest set by the operator. Setting the region of interest is one example of a predetermined trigger. A region 3b enclosed by a dashed line in a state 3 in FIG. 3 indicates a FOV region of the second FPD in a case where the first image is acquired. A state 4 in FIG. 3 illustrates an example of the second image generated from an electrical signal that is acquired by the second FPD upon reception of display of the first image. When a region of interest is set in the first image in the state 2 or the state 3, the second image illustrated in the state 4 in FIG. 3 is further displayed. The second image is an image that includes the region of interest set in the first image and that has high resolution. That is, the second image is an image that compensates for the first image. Therefore, the operator can precisely observe the region of interest in the first image without imaging the subject again. Because it is possible to omit re-imaging as described above, radiation exposure to the subject can be reduced. A compensation process of displaying another image compensating for a partial region of a certain image as described above is performed by the X-ray image acquirer 110. The compensation process performed by the X-ray image acquirer 110 will be described in detail below with reference to FIG. 4. The X-ray image acquirer 110 is one example of a controller.

Figure 4:
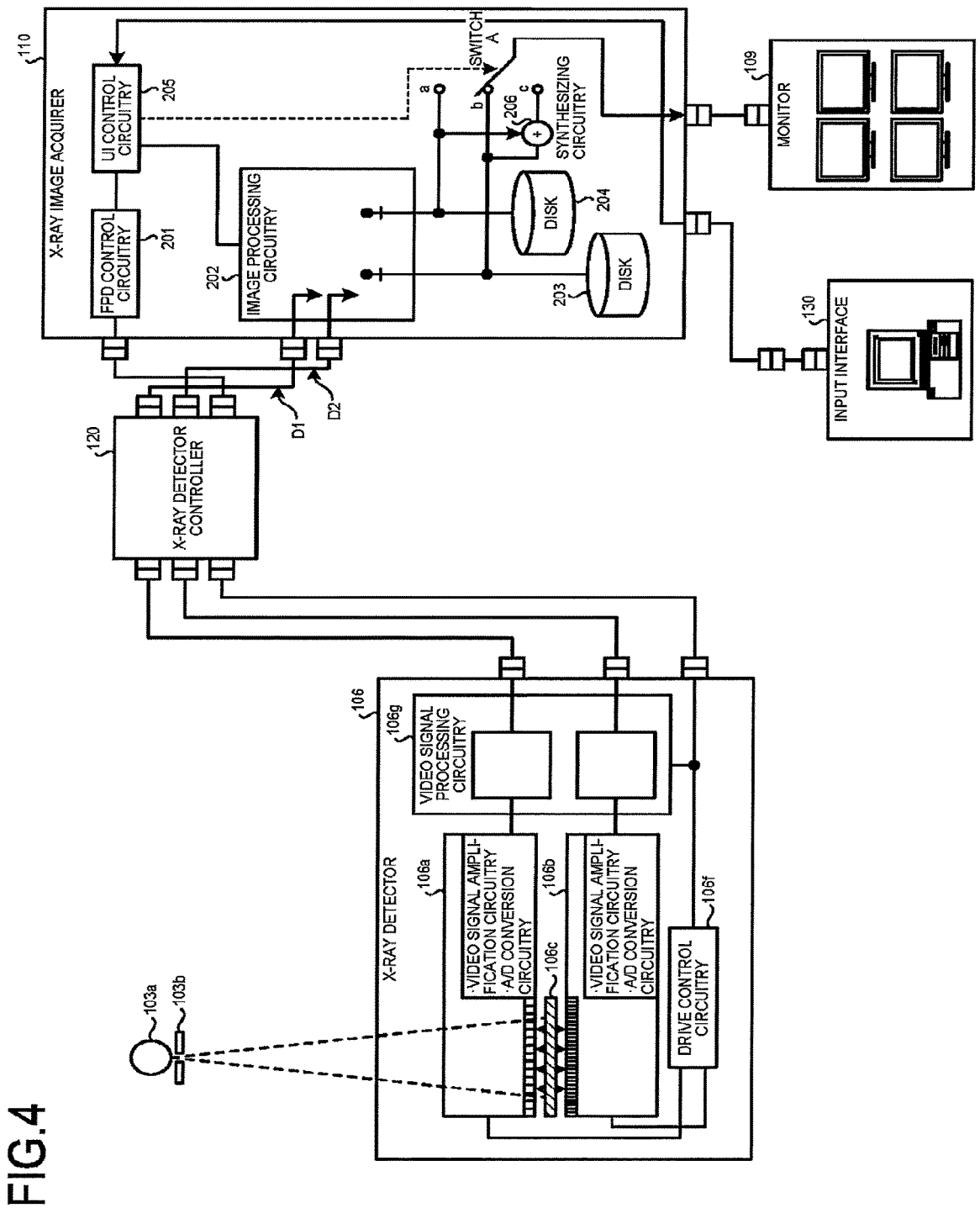
FIG. 4 is a block diagram illustrating a configuration example of an X-ray image acquirer according to the first embodiment.

FIG. 4 is a block diagram illustrating a configuration example of the X-ray image acquirer 110 according to the first embodiment. In FIG. 4, the X-ray source 103, the X-ray detector 106, the X-ray detector controller 120, the monitor 109, and the input interface 130 are also illustrated for convenience of explanation. While FIG. 2 illustrates a case in which the X-ray detector 106 includes the first photodetector 106a, the second photodetector 106b, and the scintillator 106c, the X-ray detector 106 further includes, in reality, video signal amplification circuitry and analog to digital (A/D) conversion circuitry as illustrated in FIG. 4. In the second photodetector 106b, by disposing amplification circuitry of a first stage in each of the elements and outputting an amplified signal, it becomes possible to output an electrical signal with reduced noise. It is also possible to configure A/D conversion circuitry, and in this case, the second photodetector 106b converts an accumulated electrical signal into a digital signal and outputs the digital signal. In this case, it is possible to further reduce noise. As illustrated in FIG. 4, in the X-ray detector 106, the first FPD is arranged on the X-ray source 103 side relative to the second FPD.

The X-ray detector 106 further includes drive control circuitry 106f and video signal processing circuitry 106g. The drive control circuitry 106f controls driving timing of the first photodetector 106a and the second photodetector 106b under control of the X-ray detector controller 120. The video signal processing circuitry 106g acquires an electrical signal output from the first photodetector 106a and outputs the electrical signal to the X-ray detector controller 120. The video signal processing circuitry 106g also acquires an electrical signal output from the second photodetector 106b and outputs the electrical signal to the X-ray detector controller 120.

FIG. 4 illustrates a case in which an image is transmitted from the X-ray detector controller 120 to the X-ray image acquirer 110 using a parallel system including respective data lines for the first image and the second image; however, embodiments are not limited to this example. For example, it may be possible to transmit an image from the X-ray detector controller 120 to the X-ray image acquirer 110 using a serial system including a data line shared between the first image and the second image.

As illustrated in FIG. 4, the X-ray image acquirer 110 according to the first embodiment includes FPD control circuitry 201, image processing circuitry 202, a disk 203, a disk 204, user interface (UI) control circuitry 205, and synthesizing circuitry 206.

The FPD control circuitry 201 controls, via the X-ray detector controller 120, timing at which the X-ray detector 106 reads an electrical signal. The image processing circuitry 202 performs image processing on image data output from the X-ray detector controller 120. The disk 203 stores therein an X-ray image. For example, the disk 203 is a hard disk drive (HDD), and stores therein the second image. The disk 204 stores therein an X-ray image. For example, the disk 204 is an HDD, and stores therein the first image.

For example, the image processing circuitry 202 stores image data output from the X-ray detector controller 120 in the disk 203 and the disk 204. In this case, the image processing circuitry 202 may store the first image based on output from the first detector and the second image based on output from the second detector in the disk 203 and the disk 204 in association with each other. As one example, the image processing circuitry 202 first acquires, from the X-ray detector controller 120, a combination of the first image and the second image based on X-rays that are detected simultaneously. The image processing circuitry 202 subsequently adds information for referring to the first image to the second image, and stores the second image in the disk 203. The image processing circuitry 202 also adds information for referring to the second image to the first image, and stores the first image in the disk 204.

FIG. 4 illustrates a case in which the X-ray image acquirer 110 includes the disk 203 for the second image and the disk 204 for the first image, but it may be possible to provide a single disk to be shared between the first image and the second image. The disk 203 and the disk 204 are one example of a storage. The synthesizing circuitry 206 generates a synthesized image by superimposing one of the first image and the second image on the other one of the first image and the second image.

The input interface 130 receives an instruction from the operator, and sends the received instruction to the UI control circuitry 205. The UI control circuitry 205 causes the image processing circuitry 202 to display an image for which the instruction has been received from the operator via the input interface 130. For example, upon receiving display of the first image, the UI control circuitry 205 moves the switch A to an a-side. Accordingly, the image processing circuitry 202 displays the first image on the monitor 109. For another example, upon receiving display of the second image, the UI control circuitry 205 moves the switch A to a b-side. Accordingly, the image processing circuitry 202 displays the second image on the monitor 109.

The UI control circuitry 205 receives an instruction to execute the compensation process from the operator via the input interface 130, and causes the image processing circuitry 202 to perform the compensation process. For example, upon receiving setting of a region of interest from the operator via the input interface 130 while the first image is being displayed, the UI control circuitry 205 causes the image processing circuitry 202 to perform the compensation process.

When the image processing circuitry 202 receives the instruction to perform the compensation process and displays the first image generated from an electrical signal output from the first photodetector 106a on the monitor 109, the image processing circuitry 202 further displays the second image compensating for a partial region of the first image. More specifically, when the first image is displayed on the monitor 109, and if the region of interest set in the first image is present in the FOV of the second detector 106e, the image processing circuitry 202 further displays the second image including the region of interest. That is, when the operator reviews the first image acquired in the past, and if the region of interest set in the first image is present in the FOV of the second detector 106e, the image processing circuitry 202 calls up the second image that was acquired simultaneously with the first image acquired in the past and that includes the region of interest, and displays the first image and the called up second image on the monitor 109.

Figure 5A:
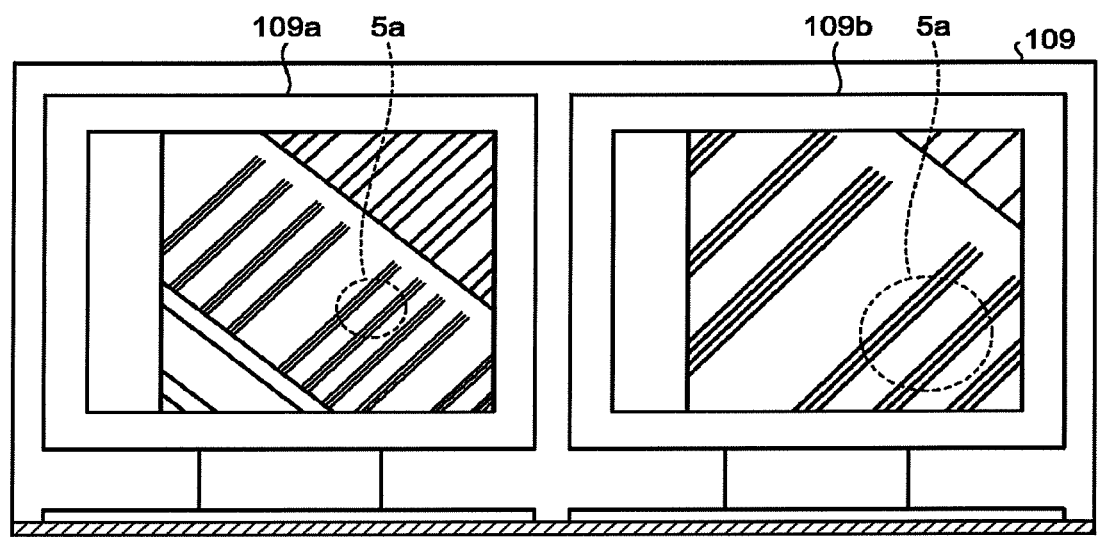
FIG. 5A is a diagram for explaining the first embodiment.
Figure 5B:
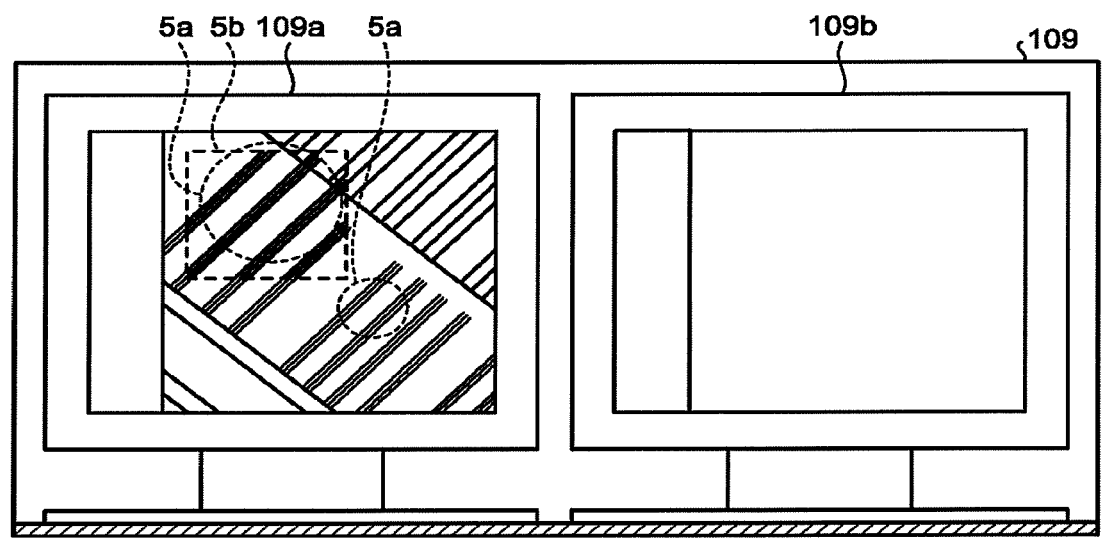
FIG. 5B is a diagram for explaining the first embodiment.

When performing the compensation process, the image processing circuitry 202 may display the first image and the second image in different display areas, or may superimpose and display the second image on the first image. FIG. 5A and FIG. 5B are diagrams for explaining the first embodiment.

FIG. 5A illustrates a case in which the first image and the second image are displayed in different display areas. In the example illustrated in FIG. 5A, the monitor 109 includes a plurality of sub monitors 109a and 109b. As illustrated in FIG. 5A, the sub monitor 109a displays the first image that is acquired upon reception of display of the first image. In this case, the UI control circuitry 205 moves the switch A illustrated in FIG. 4 to the a-side. If a region of interest 5a is set in the first image (read from the disk 204), the image processing circuitry 202 determines whether the region of interest is included in the second image. If the image processing circuitry 202 determines that the region of interest is included in the second image, the UI control circuitry 205 moves the switch A illustrated in FIG. 4 to the b-side, and the image processing circuitry 202 reads the second image including the region of interest from the disk 203 and outputs the second image to the monitor 109. Accordingly, as illustrated in FIG. 5A, the second image including the region of interest 5a is displayed on the sub monitor 109b.

FIG. 5B illustrates a case in which the second image is superimposed and displayed on the first image. In the example illustrated in FIG. 5B, the monitor 109 includes the plurality of sub monitors 109a and 109b similarly to the example illustrated in FIG. 5A. As illustrated in FIG. 5B, the sub monitor 109a displays the first image that is acquired upon reception of display of the first image. In this case, the UI control circuitry 205 moves the switch A illustrated in FIG. 4 to the a-side. If the region of interest 5a is set in the first image (read from the disk 204), the image processing circuitry 202 determines whether the region of interest is included in the second image. If the image processing circuitry 202 determines that the region of interest is included in the second image, the UI control circuitry 205 moves the switch A illustrated in FIG. 4 to a c-side. The image processing circuitry 202 outputs the first image read from the disk 204 to the synthesizing circuitry 206, reads the second image including the region of interest from the disk 203, and outputs the second image to the synthesizing circuitry 206. Accordingly, as illustrated in FIG. 5B, a synthesized image obtained by superimposing a second image 5b including the region of interest 5a on the first image is displayed on the sub monitor 109a. In other words, the X-ray image acquirer 110 superimposes and displays the second image 5b on the first image. In this case, no image is displayed on the sub monitor 109b. As a position for superimposing the second image 5b, any position can be set as long as display of a region corresponding to the region of interest 5a is not interfered with on the sub monitor 109a.

Figure 6:
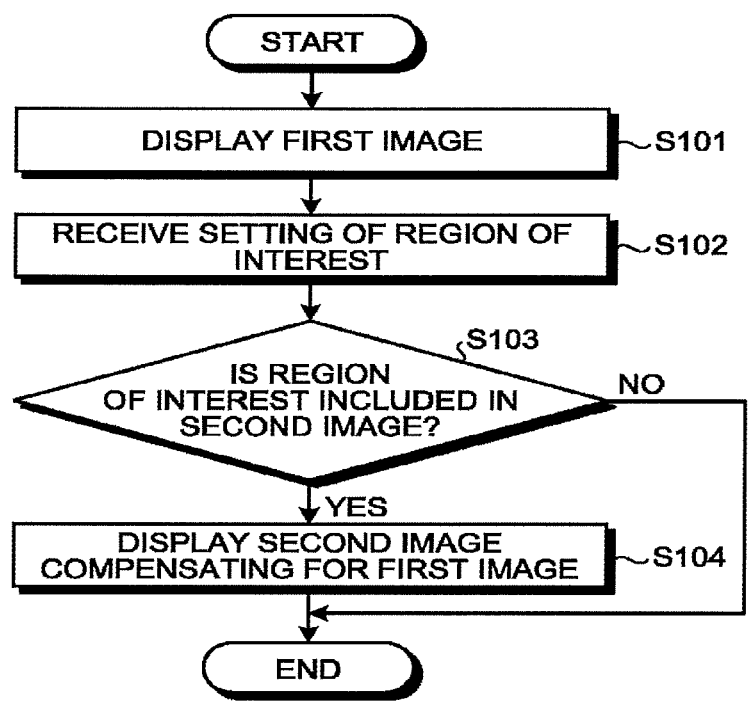
FIG. 6 is a flowchart illustrating the flow of a process performed by the X-ray image acquirer according to the first embodiment.

FIG. 6 is a flowchart illustrating the flow of a process performed by the X-ray image acquirer 110 according to the first embodiment. In FIG. 6, a flowchart for explaining entire operation of the X-ray image acquirer 110 is illustrated, and correspondence between the components and steps of the flowchart will be described below. In the following description, it is assumed that the process illustrated in FIG. 6 is performed after the first image is acquired upon reception of display of the first image.

Step S101 is a step implemented by the image processing circuitry 202. At Step S101, the image processing circuitry 202 displays the first image. Step S102 is a step implemented by the UI control circuitry 205. At Step S102, the UI control circuitry 205 receives setting of a region of interest in the first image. Accordingly, the UI control circuitry 205 causes the image processing circuitry 202 to perform the compensation process.

Step S103 is a step implemented by the image processing circuitry 202. At Step S103, the image processing circuitry 202 determines whether the region of interest is included in the second image. If the image processing circuitry 202 does not determine that the region of interest is included in the second image (No at Step S103), the process ends.

In contrast, if the image processing circuitry 202 determines that the region of interest is included in the second image (Yes at Step S103), the process proceeds to Step S104. Step S104 is a step implemented by the image processing circuitry 202. At Step S104, the image processing circuitry 202 displays the second image compensating for the first image.

As described above, in the first embodiment, the second photodetector 106b has higher resolution than the first photodetector 106a. Further, in the first embodiment, when the first image is displayed on the monitor 109, and if the region of interest set in the first image is present in the FOV of the second detector 106e, the X-ray image acquirer 110 further displays the second image including the region of interest. As a result, according to the first embodiment, when an operator desires to precisely observe the region of interest after checking the first image for example, the operator can observe the image of the region of interest with high resolution without re-acquiring the image. Further, according to the first embodiment, the operator can perform inspection efficiently because it is not necessary to re-acquire the image. Furthermore, according to the first embodiment, it is possible to reduce X-ray radiation exposure to the subject and reduce burden on the subject because it is not necessary to re-acquire the image.

In the embodiment described above, an example has been described in which the X-ray image acquirer 110 includes the synthesizing circuitry 206; however, embodiments are not limited to this example. For example, the X-ray image acquirer 110 may be configured without the synthesizing circuitry 206.

Further, the X-ray image acquirer 110 may display the whole second image, or may display a part of the second image. For example, the X-ray image acquirer 110 first determines whether the region of interest set in the first image is present in the FOV of the second detector 106e. If the region of interest is present in the FOV of the second detector 106e, the X-ray image acquirer 110 calls up the second image that is stored in association with the first image. Subsequently, the X-ray image acquirer 110 compares resolution of the second image and resolution of the monitor 109. If the resolution of the monitor 109 is higher than the resolution of the second image, the X-ray image acquirer 110 displays the whole second image on the monitor 109.

In contrast, if the resolution of the monitor 109 is lower than the resolution of the second image, the X-ray image acquirer 110 displays a part of the second image on the monitor 109. For example, the X-ray image acquirer 110 receives operation of selecting a region including the region of interest in the second image, and displays the selected region on the monitor 109. As one example, the X-ray image acquirer 110 first receives, from the operator, designation of a cropped region including a region centered at the region of interest in the second image. Subsequently, the X-ray image acquirer 110 adjusts the number of pixels of the cropped region using an enlargement ratio corresponding to a ratio between the number of pixels of the monitor 109 (matrix size) and the number of pixels of the cropped region. That is, the X-ray image acquirer 110 resizes the cropped region in accordance with the resolution of the monitor 109. The X-ray image acquirer 110 displays the adjusted cropped region on the monitor 109.

With this operation, the X-ray image acquirer 110 can provide, to the operator, the second image with the original resolution of the second image. Specifically, when the resolution of the monitor 109 is lower than the resolution of the second image, and if the entire second image is displayed on the monitor 109, the second image is displayed with resolution that is reduced in accordance with the resolution of the monitor 109. In contrast, if a part of the second image is displayed in accordance with a relationship between the resolution of the second image and the resolution of the monitor 109, the second image is displayed without changing the resolution.

In the embodiment described above, an example has been described in which when a region of interest is set while the first image is being displayed, the second image corresponding to a partial region of the first image is displayed; however, embodiments are not limited to this example.

For example, the X-ray image acquirer 110 may display the second image corresponding to a partial region of the first image if a predetermined trigger other than the setting of a region of interest occurs while the first image is being displayed. Examples of the predetermined trigger other than the setting of the region of interest include designation operation of designating a position on the first image. For example, the operator performs the designation operation by clicking a position of interest on the first image through operation of a mouse included in the input interface 130. For example, when the input interface 130 and the monitor 109 are integrated into a touch panel, the operator performs the designation operation by tapping a position of interest on the first image displayed on the touch panel.

For example, the predetermined trigger is set before the first image is displayed, and stored in a memory. For example, the X-ray image acquirer 110 reads setting information on the predetermined trigger from the memory when starting to display the first image, compares operation received from the operator and the setting information, and determines whether the predetermined trigger is received.

If the predetermined trigger is received while the first image is being displayed, the X-ray image acquirer 110 displays the second image corresponding to a partial region of the first image. For example, when a position designated on the first image is present in the FOV of the second detector 106e, the X-ray image acquirer 110 calls up the second image that is stored in association with the first image, and displays the second image.

In the embodiment described above, an example has been described in which the second image including the region of interest is further displayed in accordance with a positional relationship between the region of interest set in the first image and the FOV of the second detector 106e while the first image is being displayed on the monitor 109; however, embodiments are not limited to this example.

For example, when the region of interest set in the first image is present in the FOV of the second detector 106e, the X-ray image acquirer 110 may call up the second image that is stored in association with the first image, and display the second image instead of the first image. That is, the X-ray image acquirer 110 may display the second image instead of the first image in accordance with a positional relationship between the region of interest set in the first image and the FOV of the second detector 106e while the first image is being displayed on the monitor 109.

In the embodiment described above, an example has been described in which a past image is displayed; however, embodiments are not limited to this example. For example, the embodiment described above is applicable to a case in which an image being acquired is displayed in real time. In this case, if it is desired to simultaneously display the first image and the second image, it may be possible to simultaneously output both of the images to the respective monitors 109. When the first image and the second image are simultaneously displayed, the first detector and the second detector are switched from one to the other at an extremely high speed.

Figure 7:
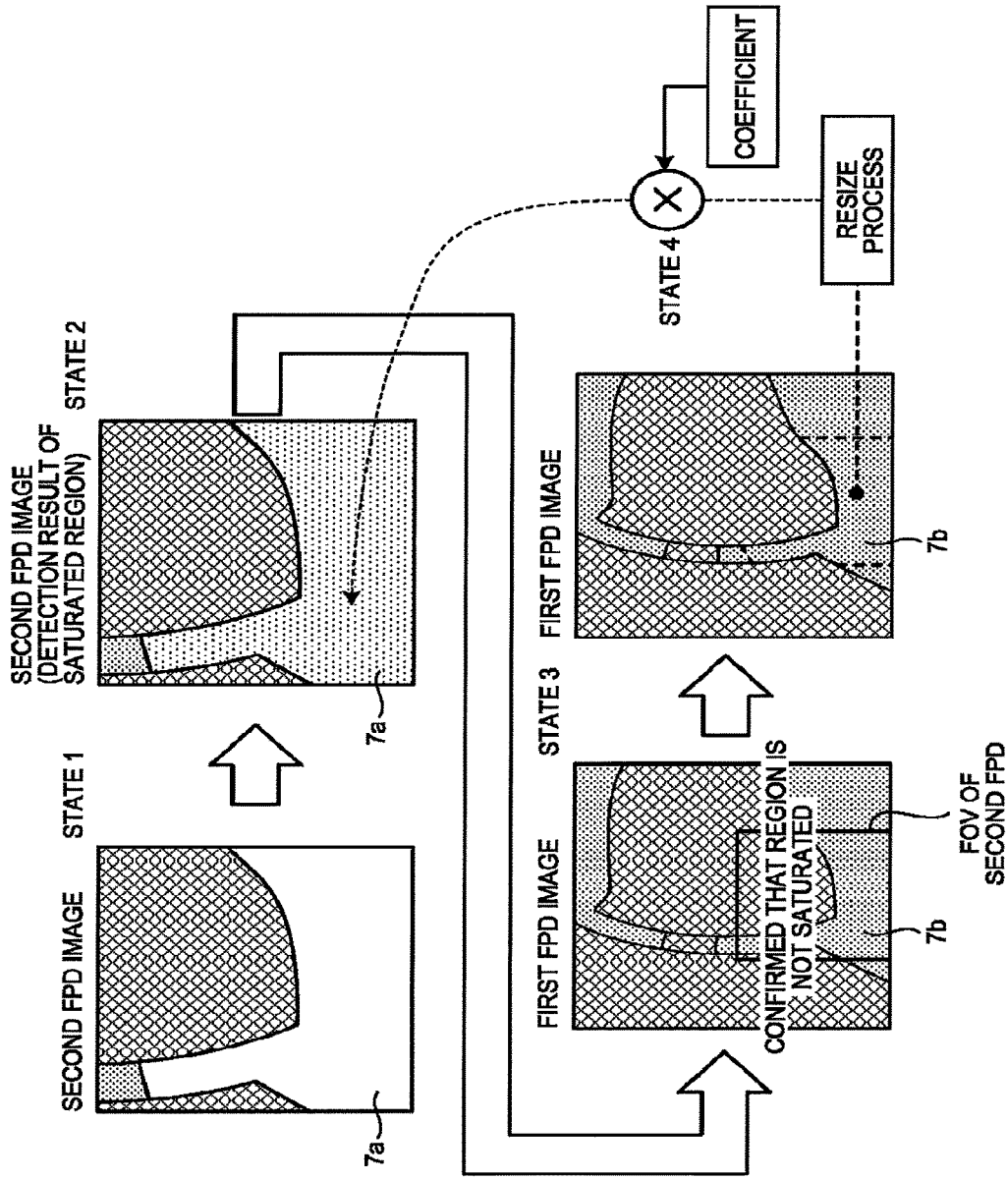
FIG. 7 is a diagram for explaining a second embodiment.

In the first embodiment, a case has been described in which the second image compensating for a partial region of the first image is displayed when the first image generated from an electrical signal output from the first photodetector 106a is displayed on the monitor 109. In a second embodiment, a case will be described in which the first image compensating for a partial region of the second image is displayed when the second image generated from an electrical signal output from the second photodetector 106b is displayed on the monitor 109. FIG. 7 is a diagram for explaining the second embodiment.

FIG. 7 illustrates a case in which display of the second image is designated by an operator via the input interface 130. A state 1 in FIG. 7 illustrates an example of the second image designated by the operator. For example, when the second FPD uses a CMOS sensor to obtain high resolution in the X-ray diagnostic apparatus 100, the second FPD has a narrower X-ray dynamic range and is more likely to cause saturation as compared to the first FPD. For example, as illustrated in the state 1 in FIG. 7, the second image may include an image saturated region 7a. It is assumed that the operator desires to check information on the image saturated region 7a.

A state 2 in FIG. 7 illustrates an example of the second image in a case where an instruction indicating a request to check the information on the image saturated region 7a is received from the operator via the input interface 130. In this case, when the second image is displayed on the monitor 109, and if the second image is saturated, the X-ray diagnostic apparatus 100 performs a compensation process of displaying the first image compensating for a saturated region of the second image. As one example, as illustrated in the state 2 in FIG. 7, the X-ray diagnostic apparatus 100 replaces the image saturated region 7a of the second image with a region 7b of the unsaturated first image corresponding to the image saturated region 7a of the second image. Explanation of the compensation process according to the second embodiment will be continued below with reference to FIG. 7.

A state 3 in FIG. 7 illustrates an example of the first image that is acquired by the first FPD when the second image is acquired. As illustrated in the state 3 in FIG. 7, the region 7b corresponding to the image saturated region$^7$a of the second image is determined in the first image, and it is confirmed that the region 7b is not saturated.

A state 4 in FIG. 7 indicates preprocessing that is performed prior to the compensation process. In the preprocessing, the region 7b used for the compensation process is set, and a resize process and a gain coefficient multiplication process are performed. As illustrated in the state 2 in FIG. 7, for example, the predetermined region 7b of the first image subjected to the preprocessing is placed as an alternative at a corresponding position in the second image. The compensation process of displaying another image compensating for a partial region of a certain image as described above is performed by an X-ray image acquirer 110a. The compensation process performed by the X-ray image acquirer 110a will be described in detail below with reference to FIG. 8. The X-ray image acquirer 110a is one example of the controller.

Figure 8:
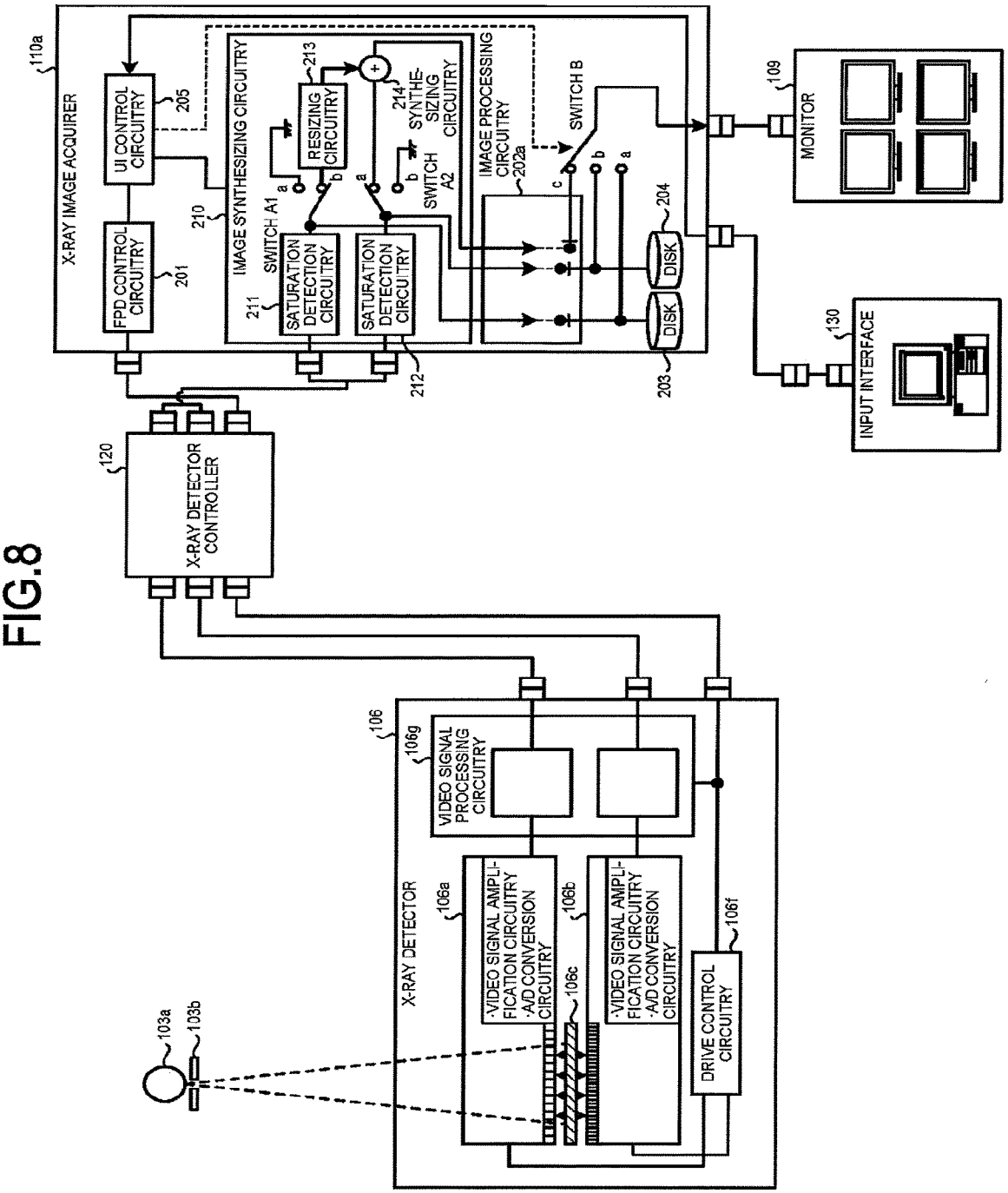
FIG. 8 is a block diagram illustrating a configuration example of an X-ray image acquirer according to the second embodiment.

The entire configuration of the X-ray diagnostic apparatus 100 according to the second embodiment is the same as the configuration example illustrated in FIG. 1 except that the X-ray image acquirer 110a has functions different from those of the X-ray image acquirer 110 of the first embodiment, and therefore, explanation thereof will be omitted. FIG. 8 is a block diagram illustrating a configuration example of the X-ray image acquirer 110a according to the second embodiment. In FIG. 8, the X-ray source 103, the X-ray detector 106, the X-ray detector controller 120, the monitor 109, and the input interface 130 are also illustrated for convenience of explanation. As illustrated in FIG. 8, in the X-ray detector 106, the first FPD is arranged on the X-ray source 103 side relative to the second FPD.

FIG. 8 illustrates a case in which an image is transmitted from the X-ray detector controller 120 to the X-ray image acquirer 110a using a serial system including a data line shared between the first image and the second image; however, embodiments are not limited to this example. For example, it may be possible to transmit an image from the X-ray detector controller 120 to the X-ray image acquirer 110a using a parallel system including respective dedicated data lines for the first image and the second image.

As illustrated in FIG. 8, the X-ray image acquirer 110a according to the second embodiment includes the FPD control circuitry 201, image processing circuitry 202a, the disk 203, the disk 204, the UI control circuitry 205, and image synthesizing circuitry 210.

The FPD control circuitry 201 controls, via the X-ray detector controller 120, timing at which the X-ray detector 106 reads an electrical signal. The image processing circuitry 202a acquires image data output from the X-ray detector controller 120 via the image synthesizing circuitry 210. The image processing circuitry 202a performs image processing on the acquired image data. The disk 203 stores therein an X-ray image. For example, the disk 203 is an HDD, and stores therein the second image. The disk 204 stores therein an X-ray image. For example, the disk 204 is an HDD, and stores therein the first image. FIG. 8 illustrates a case in which the X-ray image acquirer 110a includes the disk 203 for the second image and the disk 204 for the first image, but it may be possible to provide a single disk shared between the first image and the second image.

The input interface 130 receives an instruction from the operator, and sends the received instruction to the UI control circuitry 205. The UI control circuitry 205 causes the image processing circuitry 202 to display an image for which the instruction has been received from the operator via the input interface 130. For example, upon receiving display of the first image, the UI control circuitry 205 moves a switch B to a b-side. Accordingly, the image processing circuitry 202a displays the first image on the monitor 109. For another example, upon receiving display of the second image, the UI control circuitry 205 moves the switch B to an a-side. Accordingly, the image processing circuitry 202a displays the second image on the monitor 109.

The UI control circuitry 205 receives an instruction to execute the compensation process from the operator via the input interface 130, and causes the image processing circuitry 202a to perform the compensation process. For example, upon receiving setting of the compensation process from the operator via the input interface 130 while the second image is being displayed, the UI control circuitry 205 causes the image processing circuitry 202a to perform the compensation process. Upon receiving the instruction to perform the compensation process, for example, the image processing circuitry 202a may display the second image and the first image corresponding to the saturated region of the second image in different display areas, or may display a synthesized image in which the saturated region of the second image is replaced with the first image. The synthesized image is generated by the image synthesizing circuitry 210. Therefore, a synthesized image generation process performed by the image synthesizing circuitry 210 will be first described below, and thereafter the compensation process performed by the image processing circuitry 202a will be described in detail.

When receiving the instruction to perform the compensation process and displaying the second image generated from an electrical signal output from the second photodetector 106b on the monitor 109, the image synthesizing circuitry 210 generates a synthesized image in which a partial region of the second image is replaced with the first image. More specifically, when the image synthesizing circuitry 210 displays the second image on the monitor 109, and if the second image is saturated, the image synthesizing circuitry 210 generates a synthesized image in which the saturated region of the second image is replaced with the first image.

The image synthesizing circuitry 210 includes saturation detection circuitry 211, saturation detection circuitry 212, resizing circuitry 213, and synthesizing circuitry 214. The saturation detection circuitry 212 sends second image data output from the X-ray detector controller 120 to the image processing circuitry 202a. The saturation detection circuitry 212 receives the second image output from the X-ray detector controller 120, and determines whether the received second image is saturated. If it is determined that the second image is saturated, the saturation detection circuitry 212 moves a switch A2 to an a-side. In this case, if the first image is not saturated, the synthesizing circuitry 214 generates a synthesized image. If it is not determined that the second image is saturated, the saturation detection circuitry 212 moves the switch A2 to a b-side. In this case, the synthesizing circuitry 214 does not generate a synthesized image.

The saturation detection circuitry 211 sends first image data output from the X-ray detector controller 120 to the image processing circuitry 202a. The saturation detection circuitry 211 receives the first image output from the X-ray detector controller 120, and determines whether the received first image is saturated. If it is not determined that the first image is saturated, the saturation detection circuitry 211 moves a switch A1 to a b-side. In this case, if the second image is saturated, the synthesizing circuitry 214 generates a synthesized image. If it is determined that the first image is saturated, the saturation detection circuitry 211 moves the switch A1 to an a-side. In this case, the synthesizing circuitry 214 does not generate a synthesized image even if the second image is saturated.

When the switch A1 is moved to the b-side and the switch A2 is moved to the a-side, the resizing circuitry 213 cuts out a determined portion of the first image, and corrects a pixel pitch of the first image. For example, the pixel pitch of the first FPD is different from the pixel pitch of the second FPD. More specifically, resolution of the second photodetector 106b is higher than that of the first photodetector 106a. Therefore, the resizing circuitry 213 corrects the first image such that the pixel pitch of the first image matches the pixel pitch of the second image.

The synthesizing circuitry 214 generates a synthesized image by replacing the second image with the first image at a predetermined position in the second image. For example, the synthesizing circuitry 214 corrects the pixel pitch of the first image and replaces the saturated region of the second image with the first image. The resolution of the first image is originally low, but the first image still retains sufficiently valuable information as compared to the second image that is saturated and does not retain information; therefore, the synthesized image generation process performed by the synthesizing circuitry 214 according to the second embodiment is effective. The synthesizing circuitry 214 multiplies the first image by a coefficient corresponding to a sensitivity difference between the first photodetector 106a and the second photodetector 106b, and then performs replacement. That is, in the synthesizing process, the synthesizing circuitry 214 may perform multiplication by a gain coefficient and thereafter generate a synthesized image so that the images can be synthesized more naturally. The synthesizing circuitry 214 sends the generated synthesized image to the image processing circuitry 202a.

Figure 9A:
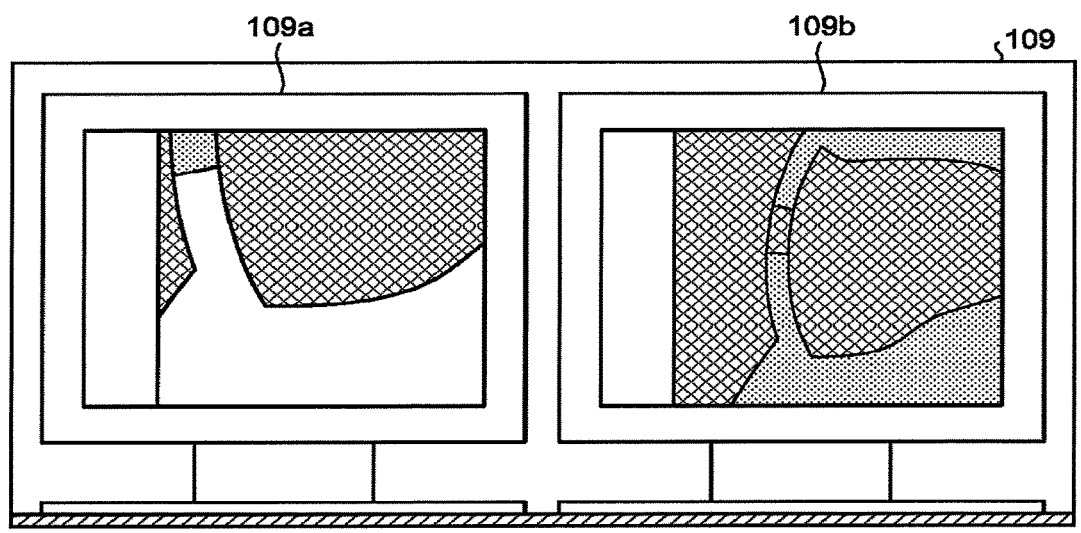
FIG. 9A is a diagram for explaining the second embodiment.
Figure 9B:
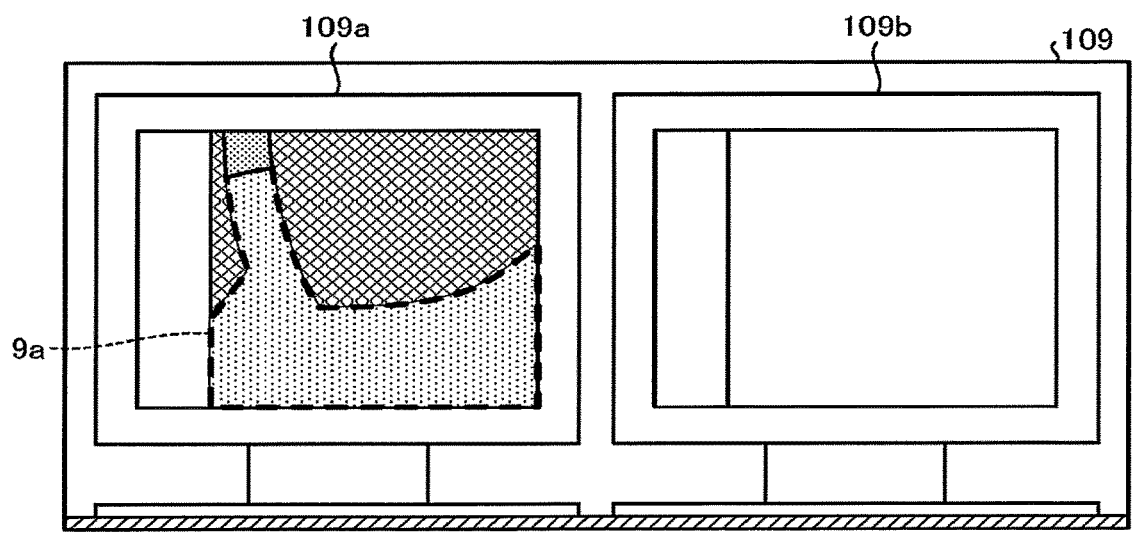
FIG. 9B is a diagram for explaining the second embodiment.

As described above, upon receiving an instruction to perform the compensation process, the image processing circuitry 202a may display the second image and the first image compensating for the saturated region of the second image in different display areas, or may display the synthesized image in which the saturated region of the second image is replaced with the first image, for example. FIG. 9A and FIG. 9B are diagrams for explaining the second embodiment.

FIG. 9A illustrates a case in which the second image and the first image compensating for the saturated region of the second image are displayed in different display areas. In the example illustrated in FIG. 9A, the monitor 109 includes the plurality of sub monitors 109a and 109b. As illustrated in FIG. 9A, the sub monitor 109a displays the second image that is acquired upon reception of display of the second image. In this case, the UI control circuitry 205 moves the switch B illustrated in FIG. 8 to the a-side. If the second image is saturated, the UI control circuitry 205 moves the switch B illustrated in FIG. 8 to the b-side. In this case, the image processing circuitry 202a outputs the first image compensating for the saturated region of the second image to the monitor 109. Accordingly, as illustrated in FIG. 9A, the first image is displayed on the sub monitor 109b.

FIG. 9B illustrates a case in which the synthesized image, in which the saturated region of the second image is replaced with the first image, is displayed. In the example illustrated in FIG. 9B, the monitor 109 includes the plurality of sub monitors 109a and 109b similarly to the example illustrated in FIG. 9A. As illustrated in FIG. 9B, the sub monitor 109a displays the second image that is acquired upon reception of display of the second image. In this case, the UI control circuitry 205 moves the switch B illustrated in FIG. 8 to the a-side. If the second image is saturated, the UI control circuitry 205 moves the switch B illustrated in FIG. 8 to a c-side. In this case, as illustrated in FIG. 9B, the image processing circuitry 202a displays the synthesized image, in which the saturated region of the second image is replaced with the first image, on the sub monitor 109a. In this case, no image is displayed on the sub monitor 109b. As illustrated in FIG. 9B, for example, the image processing circuitry 202a may further display information indicating the replaced region. FIG. 9B illustrates a case in which information 9a indicating the synthesized region is displayed in an overlaying manner.

FIG. 10 is a flowchart illustrating the flow of a process performed by the X-ray image acquirer 110a according to the second embodiment. In FIG. 10, a flowchart for explaining entire operation of the X-ray image acquirer 110a is illustrated, and correspondence between the components and steps of the flowchart will be described below. In the following description, it is assumed that the process illustrated in FIG. 10 is performed in real time when an instruction to perform the compensation process is received while the second image is being acquired. FIG. 10 illustrates a case in which the synthesized image, in which the saturated region of the second image is replaced with the first image, is displayed.

Step S201 and Step S202 are steps implemented by the saturation detection circuitry 212. At Step S201, the saturation detection circuitry 212 determines whether saturation of the second image is detected. If the saturation detection circuitry 212 does not determine that saturation of the second image is detected (No at Step S201), the process ends. In contrast, if the saturation detection circuitry 212 determines that saturation of the second image is detected (Yes at Step S201), the saturation detection circuitry 212 determines a saturated pixel (Step S202).

Step S203 and Step S204 are steps implemented by the saturation detection circuitry 211. At Step S203, the saturation detection circuitry 211 determines whether saturation of the first image is detected. If the saturation detection circuitry 211 determines that saturation of the first image is detected (Yes at Step S203), the process ends. In contrast, if the saturation detection circuitry 211 does not determine that saturation of the first image is detected (No at Step S203), the saturation detection circuitry 211 determines a pixel of the first image corresponding to the pixel determined in the second image (Step S204).

Step S205 is a step implemented by the resizing circuitry 213. At Step S205, the resizing circuitry 213 resizes the first image. Step S206 is a step implemented by the synthesizing circuitry 214. At Step S206, the synthesizing circuitry 214 generates a synthesized image. Step S207 is a step implemented by the image processing circuitry 202a. At Step S207, the image processing circuitry 202a displays the synthesized image.

As described above, in the second embodiment, the first photodetector 106a has a wider dynamic range and is less likely to be saturated as compared to the second photodetector 106b. Therefore, even if the second image is saturated, the first image may remain unsaturated in some cases. In view of this, in the second embodiment, when the second image is displayed on the monitor 109, and if the second image is saturated, the X-ray image acquirer 110a displays the first image compensating for the saturated region of the second image. In this manner, according to the second embodiment, even if the second image is saturated when the operator observes the second image for example, the operator can observe information on the saturated region of the second image by compensating for the saturated region with the first image. Further, according to the second embodiment, the operator can perform inspection efficiently because it is not necessary to re-acquire the image (due to a change in an X-ray radiation condition, or the like). Furthermore, according to the second embodiment, it is possible to reduce X-ray radiation exposure to a subject and reduce burden on the subject because it is not necessary to re-acquire the image.

In the second embodiment described above, a display mode illustrated in FIG. 9A and a display mode illustrated in FIG. 9B are described; however, embodiments are not limited to this example. For example, it may be possible to allow the image processing circuitry 202a to appropriately switch between the display mode illustrated in FIG. 9A and the display mode illustrated in FIG. 9B in accordance with an instruction from the operator.

In the second embodiment described above, an example has been described in which when the second image is displayed on the monitor 109 and if the second image is saturated, the compensation process is performed to display the first image compensating for the saturated region of the second image. In the second embodiment described above, whether the second image is saturated is determined using the second image.

Incidentally, the dynamic range of the first FPD is wider than that of the second FPD. Therefore, even if the second image is saturated, the first image may remain unsaturated in some cases. Thus, the X-ray diagnostic apparatus 100 can determine whether the second image is saturated using the first image. For example, the X-ray diagnostic apparatus 100 determines that the second image is saturated when the first image is not saturated and a pixel value of the first image is equal to or greater than a predetermined value. In view of this, in a modification of the second embodiment, a case will be described in which whether the second image is saturated is determined using the first image. In the modification of the second embodiment, if it is determined that the second image is saturated, the saturation of the second image is resolved by changing a driving rate of the second photodetector 106b.

In the modification of the second embodiment, the X-ray image acquirer 110a is the same as the X-ray image acquirer 110a of the second embodiment except that some components of the X-ray image acquirer 110a have additional functions. Therefore, in the modification of the second embodiment, only differences from the second embodiment will be described.

The saturation detection circuitry 211 receives the first image output from the X-ray detector controller 120, and determines whether the second image is saturated using the received first image. If the saturation detection circuitry 211 determines that the second image is saturated, the saturation detection circuitry 211 gives an instruction to change the driving rate of the second photodetector 106b to the FPD control circuitry 201 via the UI control circuitry 205.

Upon receiving the instruction to change the driving rate of the second photodetector 106b from the saturation detection circuitry 211 via the UI control circuitry 205, the FPD control circuitry 201 changes the driving rate of the second photodetector 106b via the X-ray detector controller 120. In other words, when it is determined that the second image is saturated, the X-ray detector controller 120 changes timing at which the second photodetector 106b reads an electrical signal. FIG. 11A and FIG. 11B are diagrams for explaining the modification of the second embodiment.

FIG. 11A illustrates a process of outputting an electrical signal from the second photodetector 106b before the timing is changed. In other words, this example indicates the timing at which the second photodetector 106b reads an electrical signal when the second image is not saturated.

When a pulsed X-ray is irradiated to acquire an X-ray image, a storage period for accumulating an electric charge that is generated while an X-ray pulse is being irradiated and a read period for reading an electric charge signal while the X-ray pulse is not being irradiated are set in the second photodetector 106b. For example, the second photodetector 106b outputs an X-ray signal by reading an electric charge signal in the readout period after the storage period. The X-ray detector controller 120 generates an X-ray image using the acquired X-ray signal.

If it is determined that the second image is saturated, the X-ray detector controller 120 changes the timing at which the second photodetector 106b reads an electrical signal. FIG. 11B illustrates a process of outputting an electrical signal from the second photodetector 106b after the timing is changed. In other words, this example illustrates the timing at which the second photodetector 106b reads an electrical signal when the second image is saturated.

As illustrated in FIG. 11B, the second photodetector 106b sequentially acquires output signals by continuously performing reading at a constant high speed in both of an X-ray incident period and an X-ray non-incident period. For example, the second photodetector 106b repeats reading of electric charge signals accumulated in the photodiode while an X-ray pulse is irradiated once, without setting the storage period. In other words, the second photodetector 106b is driven in accordance with a high-speed acquisition rate of the CMOS-FPD, and reads a single X-ray pulse in a divided manner and outputs corresponding output signals. The second photodetector 106b acquires X-ray signals among the output signals, and adds the acquired X-ray signals to obtain an X-ray signal for a single frame. Each of the output signals that are read in a divided manner from a single X-ray pulse may be referred to as a "child frame".

If it is determined that the second image is saturated, the X-ray detector controller 120 adds the "child frames" and generates a second image in a certain unit in which saturation does not occur. When the X-ray detector controller 120 adds the "child frames" and generates a second image in a certain unit in which saturation does not occur, it is possible to use a technology described in Japanese Patent Application Laid-open No. 2016-87217.

Figure 12:
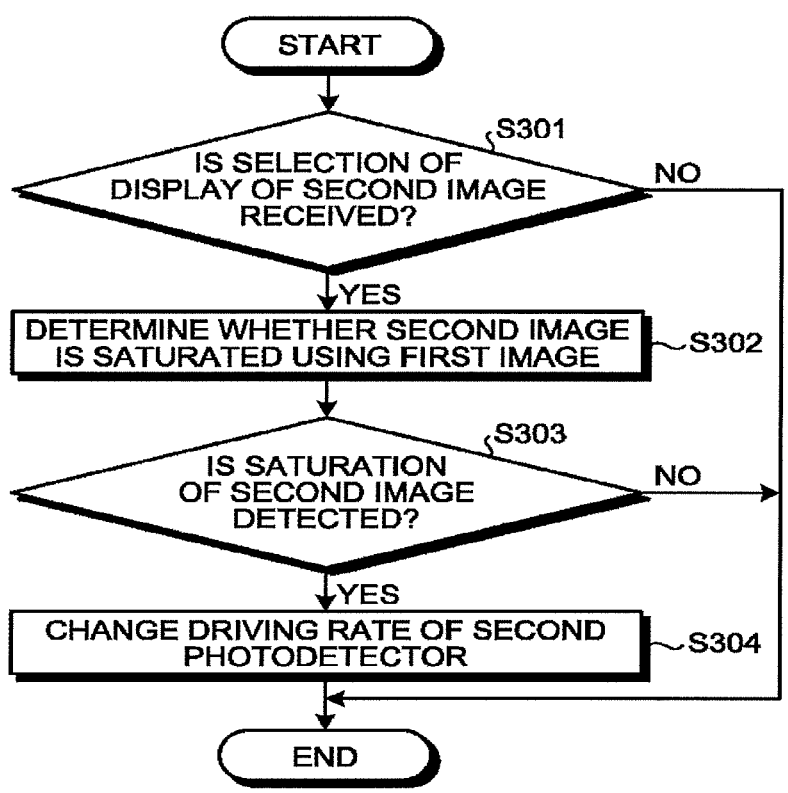
FIG. 12 is a flowchart illustrating the flow of a process performed by an X-ray image acquirer according to the modification of the second embodiment.

FIG. 12 is a flowchart illustrating the flow of a process performed by the X-ray image acquirer 110a according to the modification of the second embodiment. In FIG. 12, a flowchart for explaining entire operation of the X-ray image acquirer 110a is illustrated, and correspondence between the components and steps of the flowchart will be described below. In the following description, it is assumed that the process illustrated in FIG. 12 is performed in real time when an instruction to change the driving rate is received while the second image is being acquired.

Step S301 is a step implemented by the UI control circuitry 205. At Step S301, the UI control circuitry 205 determines whether selection of display of the second image is received. If the UI control circuitry 205 does not determine that selection of display of the second image is received (No at Step S301), the process ends. In contrast, if the UI control circuitry 205 determines that selection of display of the second image is received (Yes at Step S301), the process proceeds to Step S302.

Step S302 and Step S303 are implemented by the saturation detection circuitry 211. At Step S302, the saturation detection circuitry 211 determines whether the second image is saturated using the first image. At Step S303, the saturation detection circuitry 211 determines whether saturation of the second image is detected. If the saturation detection circuitry 211 does not determine that saturation of the second image is detected (No at Step S303), the process ends.

In contrast, if the saturation detection circuitry 211 determines that saturation of the second image is detected (Yes at Step S303), the process proceeds to Step S304. Step S304 is a step implemented by the FPD control circuitry 201. At Step S304, the FPD control circuitry 201 changes the driving rate of the second detector 106e.

As described above, in the modification of the second embodiment, the dynamic range of the first photodetector 106a is wider than that of the second photodetector 106b. Therefore, even if the second image is saturated, the first image may remain unsaturated in some cases. In view of this, in the modification of the second embodiment, the X-ray image acquirer 110 determines whether the second image is saturated using the first image. In the modification of the second embodiment, if it is determined that the second image is saturated, the X-ray image acquirer 110a changes the driving rate of the second photodetector 106b. Consequently, in the modification of the second embodiment, the X-ray detector controller 120 generates the second image without saturation. In this manner, according to the modification of the second embodiment, even if the second image is saturated when the operator observes the second image for example, the operator can observe the second image without saturation by changing the driving rate of the second photodetector 106b. Further, according to the modification of the second embodiment, the operator can perform inspection efficiently because it is not necessary to re-acquire the image. Furthermore, according to the modification of the second embodiment, it is possible to reduce X-ray radiation exposure to a subject and reduce burden on the subject because it is not necessary to re-acquire an image. Confirmation whether the second image is saturated or not may be performed by determining whether a value of each of pixels of the second image reaches a saturation value that is set in advance.

Embodiments are not limited to the embodiments described above.

In the first embodiment described above, when displaying the second image that is acquired upon reception of display of the second image, the image processing circuitry 202 may display the first image as an image that compensates for a region outside the FOV region of the second image. In this case, the image processing circuitry 202 may display the second image and the first image including the region outside the FOV region of the second image in different display areas, or display the first image including the region outside the FOV region of the second image on the second image in a synthesized manner.

In the embodiments described above, as illustrated in FIG. 4 and FIG. 8 for example, it is explained that the first FPD is arranged on the X-ray source 103 side relative to the second FPD; however, embodiments are not limited to this example. For example, the second FPD may be arranged on the X-ray source 103 side relative to the first FPD in the X-ray detector 106.

Further, in the embodiments described above, an example of displaying the first image and the second image in different display areas and an example of displaying a synthesized image in which the first image and the second image are synthesized have been described; however, embodiments are not limited to this example. For example, it may be possible to display the first image, the second image, and the synthesized image in different display areas. Alternatively, it may be possible to display any two of the first image, the second image, and the synthesized image in different display areas.

Furthermore, in the embodiments described above, it is explained that the X-ray image acquirer 110 (110a) includes a plurality of circuitries; however, embodiments are not limited to this example. For example, the X-ray image acquirer 110 (110a) may be a processor and implement the same functions as those of the X-ray image acquirer 110 illustrated in FIG. 4 and the X-ray image acquirer 110a illustrated in FIG. 8 by reading a program stored in a memory and executing the program. In this case, each of processing functions implemented by the processor is stored in the memory in the form of a computer-executable program. The processor reads each of the programs from the memory and executes the programs to thereby implement functions corresponding to each of the programs. In other words, after reading each of the programs, the processor has the same functions as those of each of the circuitries provided in the X-ray image acquirer 110 illustrated in FIG. 4 and the X-ray image acquirer 110a illustrated in FIG. 8.

The word "processor" used in the above description means, for example, a central processing unit (CPU), a graphics processing unit (GPU), or a circuit such as an application specific integrated circuit (ASIC) and a programmable logic device (for example, a simple programmable logic device (SPLD), a complex programmable logic device (CPLD), and a field programmable gate array (FPGA)). The processor reads and executes the programs stored in the memory to thereby implement the functions. The programs may be directly embedded in the circuit of the processor, instead of storing the program in the memory. In this case, the processor reads and executes the programs embedded in the circuit to thereby implement the functions. Each of the processors in the embodiments does not necessarily have to be configured as a single circuit. Alternatively, a plurality of independent circuits may be combined into a single processor that implements corresponding functions. Further, a plurality of components illustrated in FIG. 4 and FIG. 8 may be integrated into a single processor that implements corresponding functions.

The components of the apparatuses illustrated in the drawings of the embodiments described above are merely conceptual, and need not be physically configured in the manner illustrated in the drawings. In other words, specific forms of distribution and integration of the apparatuses are not limited to those illustrated in the drawings, and all or part of the apparatuses may be functionally or physically distributed or integrated in arbitrary units depending on various loads or use conditions. Further, for each processing function performed by each apparatus, all or any part of the processing function may be implemented by a CPU and a program analyzed and executed by the CPU or may be implemented as hardware by wired logic.

Further, the control method explained in the embodiments described above may be implemented by causing a computer, such as a personal computer or a workstation, to execute a control program prepared in advance. The control program may be distributed via a network, such as the Internet. The control program may be stored in a computer-readable recording medium, such as a hard disk, a flexible disk (FD), a compact disc read only memory (CD-ROM), a magneto-optical disk (MO), or a digital versatile disk (DVD), and may be executed by the computer by being read from the recording medium.

According to at least one of the embodiments described above, it is possible to compensate for a partial region of an image to be displayed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
   an X-ray detector including a first detector and a second detector configured to simultaneously detect X-rays irradiated from an X-ray tube; and
   processing circuitry configured to, when displaying one of a first image based on output from the first detector and a second image based on output from the second detector on a display, display the other one of the first image and the second image corresponding to a partial region of the one of the first image and the second image,
   wherein the second detector is positioned with respect to the first detector such that (i) a detection region of the second detector overlaps with a detection region of the first detector in a first region, and (ii) the detection region of the first detector and the detection region of the second detector do not overlap in second and third regions located on opposite sides of the first region.

2. The X-ray diagnostic apparatus according to claim 1, wherein
   the X-ray detector includes:
   a scintillator configured to convert an X-ray into light; and
   a first photodetector and a second photodetector configured to share the scintillator and detect light converted by the scintillator,
   the first detector includes the scintillator and the first photodetector,
   the second detector includes the scintillator and the second photodetector, and
   the first photodetector and the second photodetector simultaneously detect light converted from X-rays by the scintillator.

3. The X-ray diagnostic apparatus according to claim 2, wherein the scintillator is arranged so as to be sandwiched between the first photodetector and the second photodetector.

4. The X-ray diagnostic apparatus according to claim 2, wherein the first photodetector has a larger field of view than the second photodetector.

5. The X-ray diagnostic apparatus according to claim 1, wherein
   the second detector has higher resolution than the first detector, and
   the processing circuitry, when displaying the first image on the display, further displays the second image including a region of interest set in the first image in accordance with a positional relationship between the region of interest and a field of view of the second detector.

6. The X-ray diagnostic apparatus according to claim 5, wherein the processing circuitry displays the first image and the second image in different display areas.

7. The X-ray diagnostic apparatus according to claim 5, wherein the processing circuitry superimposes and displays the second image on the first image.

8. The X-ray diagnostic apparatus according to claim 1, wherein
   the first detector has a wider dynamic range than the second detector, and
   when the processing circuitry displays the second image on the display, if the second image is saturated, the processing circuitry displays the first image corresponding to a saturated region of the second image.

9. The X-ray diagnostic apparatus according to claim 8, wherein when the processing circuitry displays the second image on the display, if the second image is saturated, the processing circuitry displays a synthesized image in which the saturated region of the second image is replaced with the first image.

10. The X-ray diagnostic apparatus according to claim 9, wherein
    the second detector has higher resolution than the first detector, and
    the processing circuitry corrects a pixel pitch of the first image and replaces the saturated region of the second image with the corrected first image.

11. The X-ray diagnostic apparatus according to claim 9, wherein the processing circuitry multiplies the first image by a coefficient that corresponds to a sensitivity difference between the first detector and the second detector, and replaces the second image with the multiplied first image.

12. The X-ray diagnostic apparatus according to claim 9, wherein the processing circuitry further displays information indicating a replaced region.

13. The X-ray diagnostic apparatus according to claim 8, wherein the processing circuitry displays the second image and the first image corresponding to the saturated region of the second image in different display areas.

14. An X-ray diagnostic apparatus comprising:
    an X-ray detector including:
    a scintillator configured to convert an X-ray irradiated from an X-ray tube into light; and
    a first photodetector and a second photodetector configured to share the scintillator and detect electrical signals by detecting light converted by the scintillator; and
    processing circuitry configured to display one of a first image generated from an electrical signal output from the first photodetector and a second image generated from an electrical signal output from the second photodetector on a display, wherein
    the processing circuitry determines whether the second image is saturated using the first image, and when determining that the second image is saturated, changes a driving rate of the second photodetector.

15. The X-ray diagnostic apparatus according to claim 14, wherein the first photodetector has higher detection sensitivity than the second photodetector.

16. An X-ray diagnostic apparatus comprising:
an X-ray detector including a first detector and a second detector configured to simultaneously detect X rays irradiated from an X-ray tube; and
processing circuitry configured to store a first image based on output from the first detector and a second image based on output from the second detector in a storage in association with each other,
wherein the second detector is positioned with respect to the first detector such that (i) a detection region of the second detector overlaps with a detection region of the first detector in a first region, and (ii) the detection region of the first detector and the detection region of the second detector do not overlap in second and third regions located on opposite sides of the first region.

17. The X-ray diagnostic apparatus according to claim 16, wherein
the X-ray detector includes:
a scintillator configured to convert an X-ray into light; and
a first photodetector and a second photodetector configured to share the scintillator and detect light converted by the scintillator,
the first detector includes the scintillator and the first photodetector,
the second detector includes the scintillator and the second photodetector, and
the first photodetector and the second photodetector simultaneously detect light converted from X-rays by the scintillator.

18. The X-ray diagnostic apparatus according to claim 16, wherein when displaying one of the first image and the second image on a display, the processing circuitry displays the other one of the first image and the second image corresponding to a partial region of the one of the first image and the second image, instead of the one of the first image and the second image, in response to a predetermined trigger.

19. The X-ray diagnostic apparatus according to claim 16, wherein
the second detector has higher resolution than the first detector, and
the processing circuitry, when displaying the first image on the display, displays the second image instead of the first image in accordance with a positional relationship between a region of interest set in the first image and a field of view of the second detector.

20. The X-ray diagnostic apparatus according to claim 16, wherein
the second detector has higher resolution than the first detector, and
the processing circuitry, when displaying the first image on the display, displays a part or whole of the second image in accordance with a positional relationship between a region of interest set in the first image and a field of view of the second detector and a relationship between resolution of the second image and resolution of the display.

* * * * *